United States Patent
Troitino Lopez et al.

(10) Patent No.: US 10,401,267 B2
(45) Date of Patent: Sep. 3, 2019

(54) ADDITIVE MANUFACTURING TEST FEATURE INCLUDING POWDER SAMPLING CAPSULE

(71) Applicant: General Electric Company, Schenectady, NY (US)

(72) Inventors: Jose Troitino Lopez, Greenville, SC (US); Tiffany Muller Craft, Simpsonville, SC (US); Donnell Eugene Crear, Simpsonville, SC (US); Kassy Moy Hart, Greenville, SC (US); Kamilla Koenig-Urban, Wettingen (CH); Eric Eicher McConnell, Easley, SC (US); Danijel Medved, Villmergen (CH)

(73) Assignee: General Electric Company, Schenectady, NY (US)

( * ) Notice: Subject to any disclaimer, the term of this patent is extended or adjusted under 35 U.S.C. 154(b) by 304 days.

(21) Appl. No.: 15/490,179

(22) Filed: Apr. 18, 2017

(65) Prior Publication Data
US 2018/0299359 A1     Oct. 18, 2018

(51) Int. Cl.
*B29C 64/00*      (2017.01)
*G01N 1/44*       (2006.01)
(Continued)

(52) U.S. Cl.
CPC ............. *G01N 1/44* (2013.01); *B29C 64/00* (2017.08); *B33Y 10/00* (2014.12); *B33Y 40/00* (2014.12);
(Continued)

(58) Field of Classification Search
CPC .. G01N 1/44; G01N 1/04; G01N 3/02; G01N 2203/0298; G01N 3/00; B33Y 40/00
See application file for complete search history.

(56) References Cited

U.S. PATENT DOCUMENTS

| | | |
|---|---|---|
| 9,109,979 B2 | 8/2015 | Dietrich et al. |
| 9,188,148 B2 | 11/2015 | Diehl et al. |
| 2016/0054205 A1* | 2/2016 | O'Neill .................. G01N 1/286 73/863 |

FOREIGN PATENT DOCUMENTS

EP     1486317 B1     8/2008

OTHER PUBLICATIONS

Renishaw, 2016, Investigating the effects of multiple re-use of Ti6Al4V powder in AM (Year: 2016).*

* cited by examiner

*Primary Examiner* — Eric S. McCall
*Assistant Examiner* — Timothy P Graves
(74) *Attorney, Agent, or Firm* — Dale Davis; Hoffman Warnick LLC (57) ABSTRACT

A test feature is disclosed that is formed during metal powder additive manufacturing of a production part. The test feature may include a metal powder sample capsule including a chamber for capturing unfused powder from the metal powder additive manufacturing, and a removable cap closing an end of the chamber. Alternatively, a test feature may include a quality control (QC) part, and at least one additional test element including a metal powder sample capsule integrally coupled to the QC part and including a chamber for capturing unfused powder from the metal powder additive manufacturing. The QC part is identical to the production part excepting the at least one test element. The QC part and the at least one test element are formed during the same metal powder additive manufacturing as the production part.

11 Claims, 12 Drawing Sheets

(51) Int. Cl.
  *B33Y 80/00* (2015.01)
  *B33Y 10/00* (2015.01)
  *B33Y 40/00* (2015.01)
  *G01N 3/02* (2006.01)
  *G01N 1/04* (2006.01)
  *G01N 1/10* (2006.01)
(52) U.S. Cl.
  CPC ............... *B33Y 80/00* (2014.12); *G01N 1/04* (2013.01); *G01N 3/02* (2013.01); *G01N 2001/1006* (2013.01); *G01N 2203/0298* (2013.01)

ADDITIVE MANUFACTURING TEST FEATURE INCLUDING POWDER SAMPLING CAPSULE

BACKGROUND OF THE INVENTION

The disclosure relates generally to additive manufacturing, and more particularly, to a quality control test feature including a metal powder sample capsule for metal powder additive manufacturing.

The pace of change and improvement in the realms of power generation, aviation, and other areas has accompanied extensive research for manufacturing components used in these fields. Conventional manufacture of metallic components generally includes milling or cutting away regions from a slab of metal before treating and modifying the cut metal to yield a part, which may have been simulated using computer models, and drafting software. Manufactured components which may be formed from metal can include, for example, airfoil components for installation in a turbomachine such as an aircraft engine or power generation system. The development of additive manufacturing, also known in the art as "3D printing," can reduce manufacturing costs by allowing such components to be formed more quickly, with unit-to-unit variations as appropriate. Some devices fabricated via additive manufacture can be formed initially as several distinct components at respective processing stages before being assembled in a subsequent process. Among other advantages, additive manufacture can directly apply computer-generated models to a manufacturing process while relying on less expensive, and/or raw materials.

Figure 1:
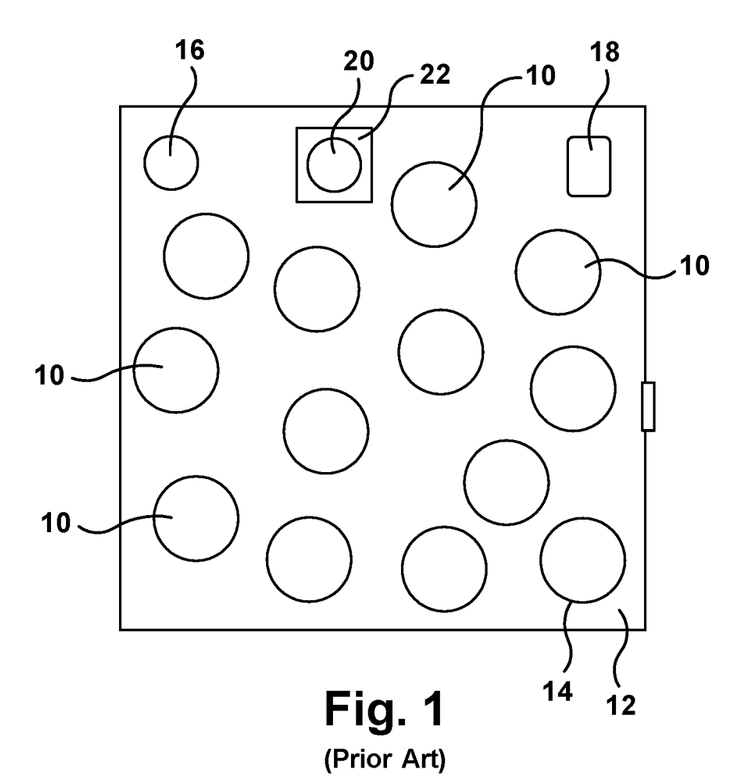
FIG. 1 shows a plan, schematic view of a conventional build platform including a number of conventional test features.

Some forms of additive manufacturing (AM) allow a component to be formed from a bed of fine metal powder positioned on a build platform, which is processed by an electron beam or laser (for example, using heat treatment such as sintering) to form a component or sub-component. One challenge with respect to AM using metal powder, and especially processes that reuse metal powder, is ensuring quality of the part being built. As shown in FIG. 1, conventionally, a number of test features 14, 16, 18, 20 for testing various aspects are additively manufactured with one or more production parts 10 (shown as round structures) on a single build platform 12 using the same build parameters, e.g., up skin, down skin, hatch, etc. The test features may be used to track powder and metal compliance with the AM specifications and part quality. For example, a quality control part 14 identical to production part 10 may be built for metallographic evaluation; a tensile bar 16 (wider outer ends with narrow middle) may be built to allow for mechanical property testing; a cylindrical or rectangular test bar 18, equal to the height of production part 10, may be used to record downtime witness features and to measure surface roughness and/or hardness; and a powder sample capsule 20 may be built to capture a sample of unfused metal powder for powder quality retention and analysis of powder chemistry and particle size.

The test features present a number of challenges. For example, each test feature 14, 16, 18, 20 is built simultaneously with but separate from production parts 10 and separate from one another. Accordingly, each test feature takes up valuable space on build platform 12, and consequently may reduce the quantity of production parts 10 printed on the build platform. Additionally, making each test feature takes time away from manufacturing the production parts, and uses valuable metal powder. With specific regard to powder sample capsule 20, additional challenges include providing sufficient support for the capsule. Typically, the capsule is built on a large foundation 22 on build platform 12. Current practice to remove the capsule from the platform requires wire electro-discharge machining (EDM), which can damage the capsule. Further, conventional capsules must be mechanically cut open, which can present handling issues for the metal powder, e.g., spillage, air distribution, etc. The described challenges can render the metal powder sample unusable for testing, e.g., due to exposure and/or contamination.

BRIEF DESCRIPTION OF THE INVENTION

A first aspect of the disclosure provides a test feature formed during metal powder additive manufacturing of a production part, the test feature including: a metal powder sample capsule including a chamber for capturing unfused powder from the metal powder additive manufacturing; and a removable cap closing an end of the chamber.

A second aspect of the disclosure provides a test feature formed during metal powder additive manufacturing of a production part, the test feature including: a quality control (QC) part; and at least one additional test element including a metal powder sample capsule integrally coupled to the QC part and including a chamber for capturing unfused powder from the metal powder additive manufacturing, wherein the QC part is identical to the production part excepting the at least one test element, the QC part and the at least one test element formed during the same metal powder additive manufacturing as the production part.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

As indicated above, the disclosure provides a test feature for metal powder additive manufacturing. The test feature is formed during metal powder additive manufacturing of a production part, and may include various test elements that allow for testing the metal powder and a number of characteristics of the additive manufacturing that may impact the production part's quality. For example, in one embodiment, the test feature includes a metal powder sample capsule including a chamber for capturing unfused powder from the metal powder additive manufacturing. The test feature may include a removable cap closing an end of the chamber. In another example, the test feature may include a quality control (QC) part having at least one test element, such as a metal powder sample capsule, integrally coupled thereto. A test feature according to the disclosure is formed during the same metal powder additive manufacturing as the production part. The QC part is identical to the production part, excepting the test elements such as the capsule, and can be used to conduct various quality control tests.

As used herein, metal powder additive manufacturing (AM) may include any process of producing a production part through the successive layering of fused or sintered metal powder rather than the removal of material, which is the case with conventional processes. Metal powder additive manufacturing can create complex geometries without the use of any sort of tools, molds or fixtures, and with little or no waste material. Instead of machining components from solid billets of plastic or metal, much of which is cut away and discarded, the only material used in additive manufacturing is what is required to shape the part. Metal powder AM processes may include but are not limited to: direct digital manufacturing (DDM), selective laser melting (SLM) and direct metal laser melting (DMLM). For purposes of description, DMLM will be described.

Figure 2:
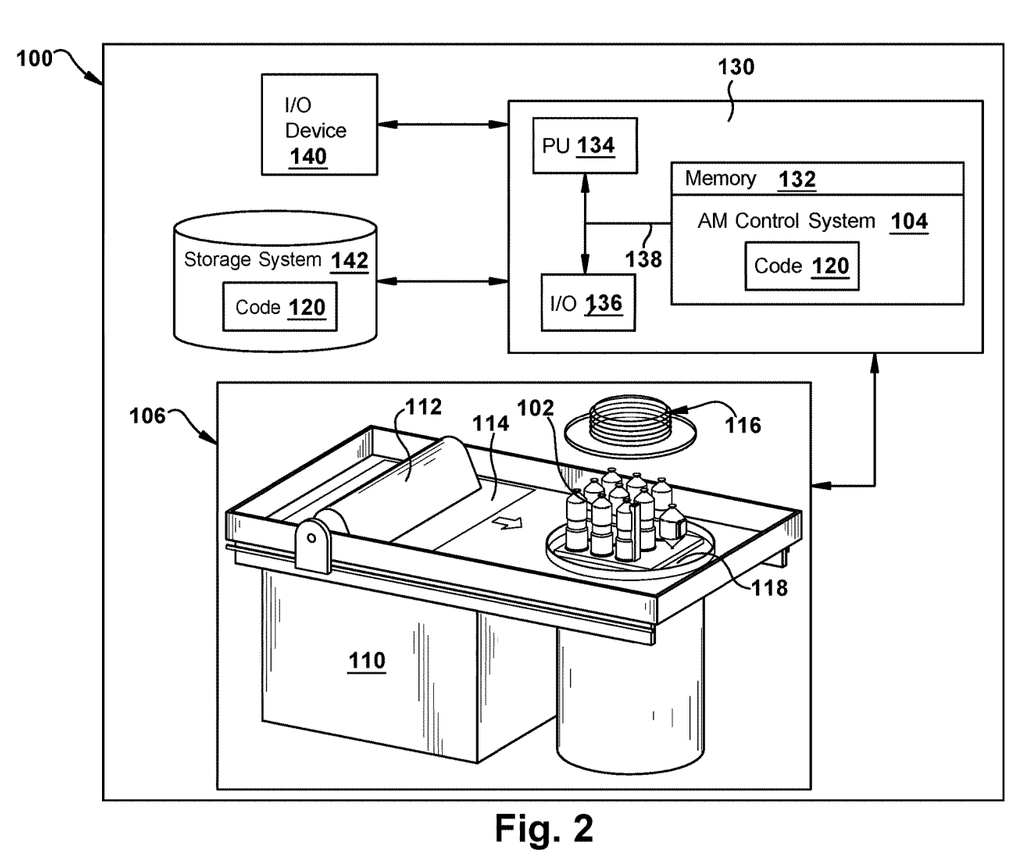
FIG. 2 shows a block diagram of an additive manufacturing process including a non-transitory computer readable storage medium storing code representative of a production part and a test feature according to embodiments of the disclosure.

To illustrate an example of metal powder AM process, FIG. 2 shows a schematic/block view of an illustrative computerized additive manufacturing system 100 for generating production parts 102 and test feature(s) 108. In this example, system 100 is arranged for DMLM. It is understood that the general teachings of the disclosure are equally applicable to other forms of additive manufacturing. Production parts 102 and a quality control part 310 (FIGS. 18-19) are illustrated as a fuel injection nozzle; however, it is understood that the additive manufacturing process can be readily adapted to manufacture any metal part.

AM system 100 generally includes a computerized additive manufacturing (AM) control system 104 and an AM printer 106. AM system 100, as will be described, executes code 120 that includes a set of computer-executable instructions defining production parts 102 and test feature(s) 108 (FIGS. 4-19) to physically generate the production parts using AM printer 106. Each AM process may use different raw materials in the form of, for example, fine-grain metal powder, a stock of which may be held in a chamber 110 of AM printer 106. In the instant case, production parts 102 and test features 108, 308 may be made of a nickel alloy or similar materials. As illustrated, an applicator 112 may create a thin layer of raw material 114 spread out as the blank canvas from which each successive slice of the final production parts 102 will be created. In other cases, applicator 112 may directly apply or print the next layer onto a previous layer as defined by code 120, e.g., in a metal binder jetting process is used. In the example shown, a laser or electron beam 116 fuses particles for each slice, as defined by code 120. Various parts of AM printer 106 may move to accommodate the addition of each new layer, e.g., a build platform 118 may lower and/or chamber 110 and/or applicator 112 may rise after each layer.

AM control system 104 is shown implemented on computer 130 as computer program code. To this extent, computer 130 is shown including a memory 132, a processor 134, an input/output (I/O) interface 136, and a bus 138. Further, computer 130 is shown in communication with an external I/O device/resource 140 and a storage system 142. In general, processor 134 executes computer program code, such as AM control system 104, that is stored in memory 132 and/or storage system 142 under instructions from code 120 representative of production parts 102 and test feature(s) 108, 308 (FIGS. 4-19), described herein. While executing computer program code, processor 134 can read and/or write data to/from memory 132, storage system 142, I/O device 140 and/or AM printer 106. Bus 138 provides a communication link between each of the components in computer 130, and I/O device 140 can comprise any device that enables a user to interact with computer 130 (e.g., keyboard, pointing device, display, etc.). Computer 130 is only representative of various possible combinations of hardware and software. For example, processor 134 may comprise a single processing unit, or be distributed across one or more processing units in one or more locations, e.g., on a client and server. Similarly, memory 132 and/or storage system 142 may reside at one or more physical locations. Memory 132 and/or storage system 142 can comprise any combination of various types of non-transitory computer readable storage medium including magnetic media, optical media, random access memory (RAM), read only memory (ROM), etc. Computer 130 can comprise any type of computing device such as a network server, a desktop computer, a laptop, a handheld device, a mobile phone, a personal data assistant, etc.

Additive manufacturing processes begin with a non-transitory computer readable storage medium (e.g., memory 132, storage system 142, etc.) storing code 120 representative of production parts 102 and test feature(s) 108, 308 (FIGS. 4-19). As noted, code 120 includes a set of computer-executable instructions defining production parts 102 and test feature(s) 108, 308 (FIGS. 4-19) that can be used to physically generate the production parts and the test features, upon execution of the code by system 100. For example, code 120 may include a precisely defined 3D model of production parts 102 and test features 108, 308 (FIGS. 4-19) and can be generated from any of a large variety of well known computer aided design (CAD) software systems such as AutoCAD®, TurboCAD®, DesignCAD 3D Max, etc. In this regard, code 120 can take any now known or later developed file format. For example, code 120 may be in the Standard Tessellation Language (STL) which was created for stereolithography CAD programs of 3D Systems, or an additive manufacturing file (AMF), which is an American Society of Mechanical Engineers (ASME) standard that is an extensible markup-language (XML) based format designed to allow any CAD software to describe the shape and composition of any three-dimensional production parts to be fabricated on any AM printer. Code 120 may be translated between different formats, converted into a set of data signals and transmitted, received as a set of data signals and converted to code, stored, etc., as necessary. Code 120 may be an input to system 100 and may come from a part designer, an intellectual property (IP) provider, a design company, the operator or owner of system 100, or from other sources. In any event, AM control system 104 executes code 120, dividing production parts 102 and test feature(s) 108, 308 (FIGS. 4-19) into a series of thin slices that it assembles using AM printer 106 in successive layers of powder. In the DMLM example, each layer is melted to the exact geometry defined by code 120 and fused to the preceding layer. Subsequently, the production parts 102 (e.g., FIGS. 2, 4) may be exposed to any variety of finishing processes, e.g., minor machining, sealing, polishing, assembly to another part, etc. Further, as will be described herein, test feature(s) 108 may be exposed to a variety of testing to evaluate the quality of production parts 102.

Figure 3:
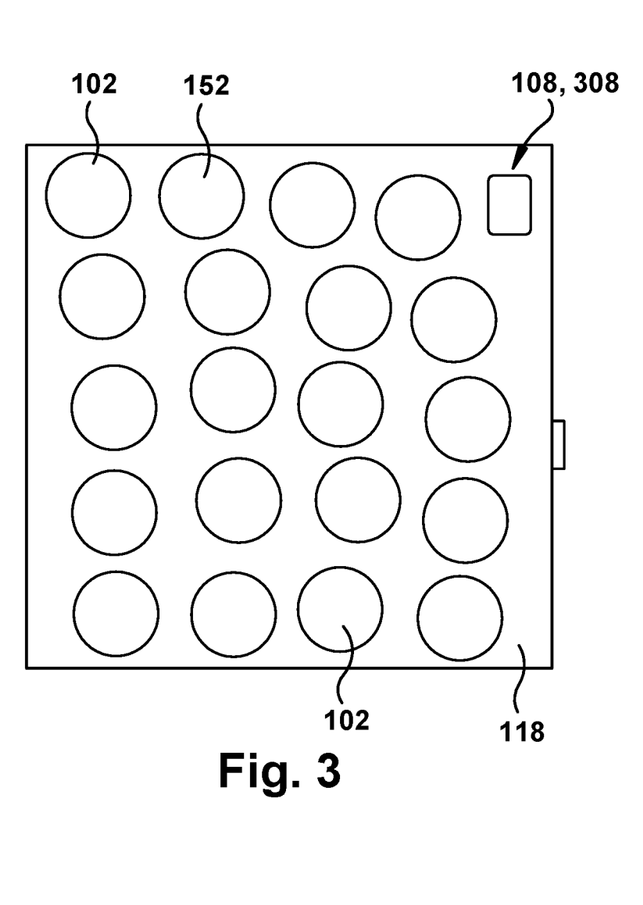
FIG. 3 shows a plan, schematic view of a build platform including a test feature according to embodiments of the disclosure.
Figure 4:
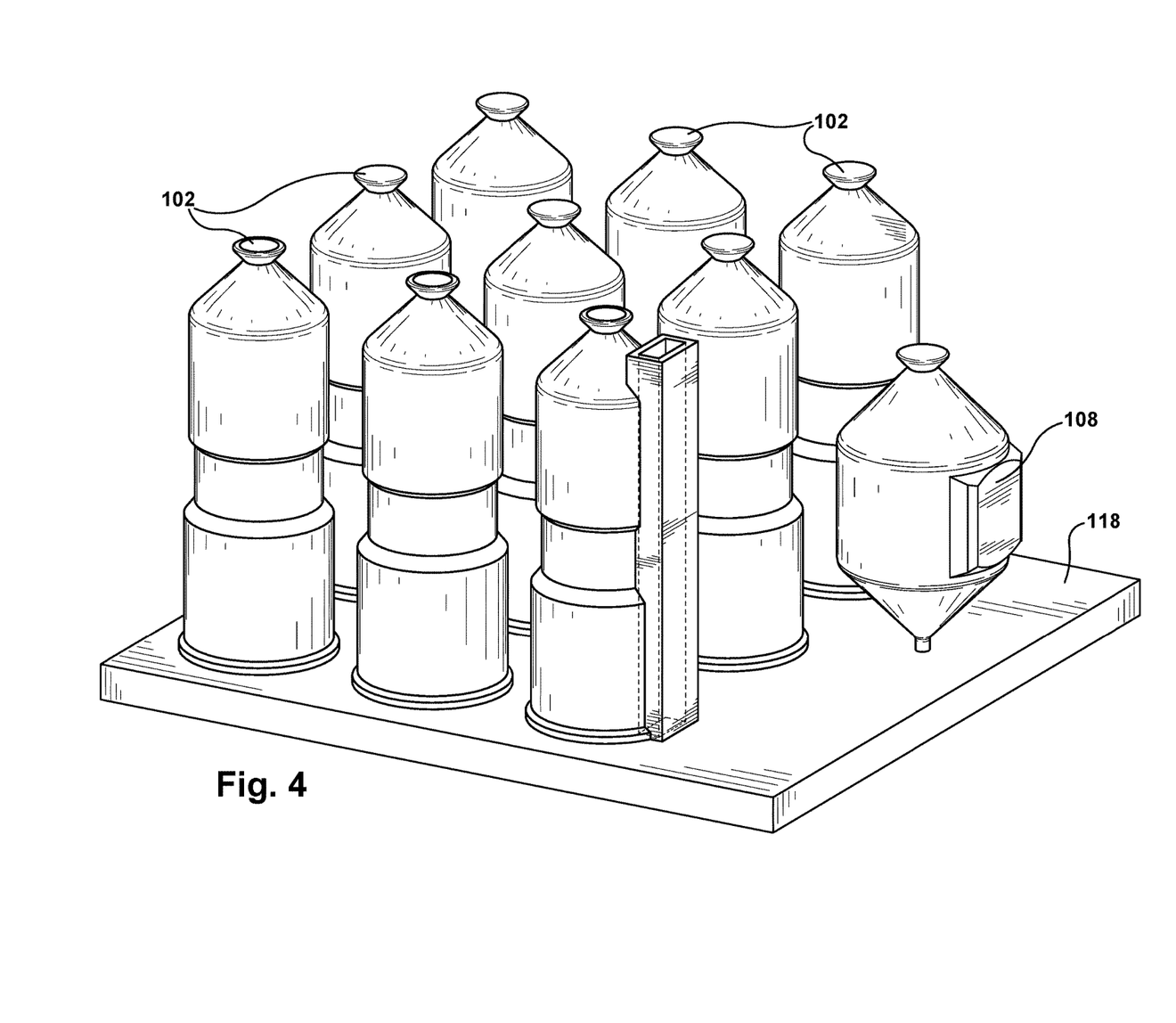
FIG. 4 shows a top, perspective view of a build platform including a test feature according to embodiments of the disclosure.

FIG. 3 shows a plan, schematic view and FIG. 4 shows a top, perspective view of a build platform 118 after AM of production parts 102 and test feature 108 and/or 308 according to embodiments of the disclosure. (Note, FIG. 4 shows both test feature 108 and 308, but in some embodiments only one would be necessary or desired). As illustrated, build platform 118 includes a plurality of production parts 102. In order to perform quality control evaluations of production parts 102, test feature 108, 308 according to embodiments of the disclosure may be built simultaneously with production parts 102.

Figure 5:
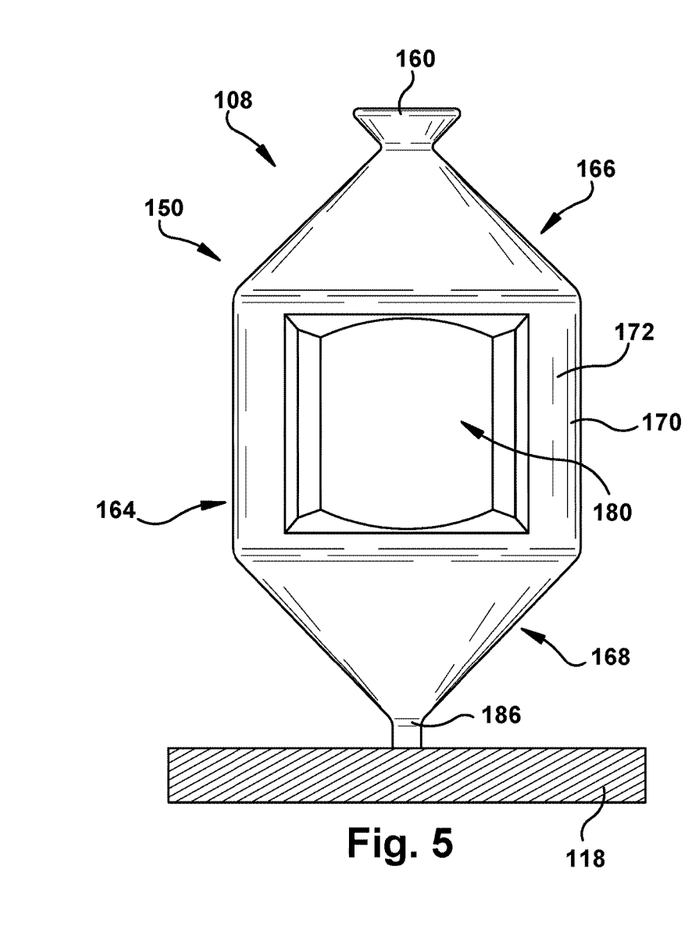
FIG. 5 shows a side view of a test feature according to an embodiment of the disclosure.
Figure 6:
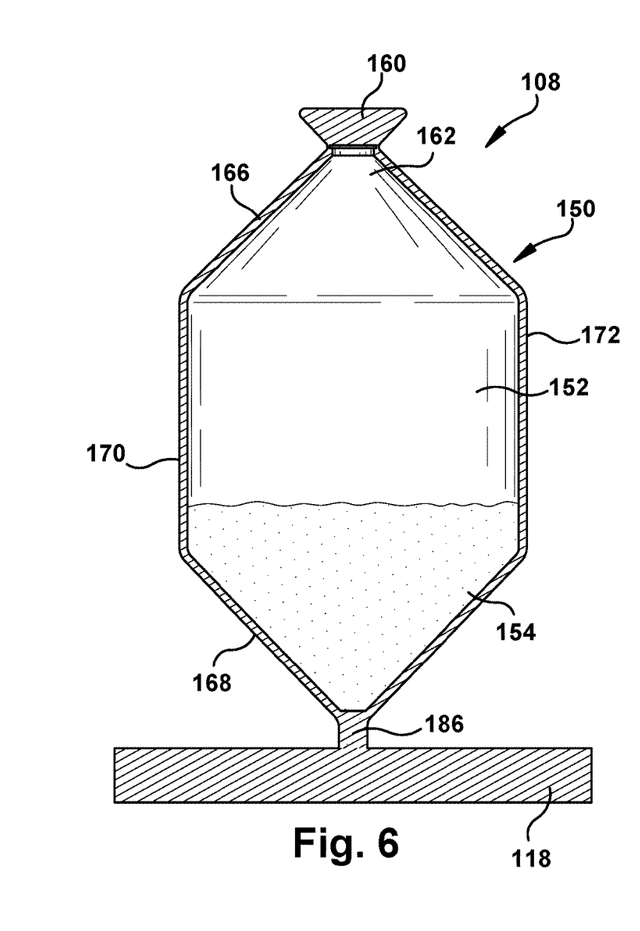
FIG. 6 shows a cross-sectional view of the test feature of FIG. 5 according to an embodiment of the disclosure.

Referring to FIGS. 5-17, a test feature can take a variety of forms according to embodiments of the disclosure. As shown in FIGS. 5 and 6, in one embodiment, test feature 108 may include a metal powder sample capsule 150 including a chamber 152 for capturing unfused metal powder 154 from the metal powder additive manufacturing (FIG. 2). That is, capsule 150 captures unfused powder from build platform 118 as additive manufacturing progresses. Unfused metal powder 154 may include metal powder not impacted by laser or electron beam 116 and as provided from chamber 110 and distributed by applicator 112. As will be described in greater detail herein, test feature 108 may also include a removable cap 160 closing an end 162 of chamber 152.

Figure 9:
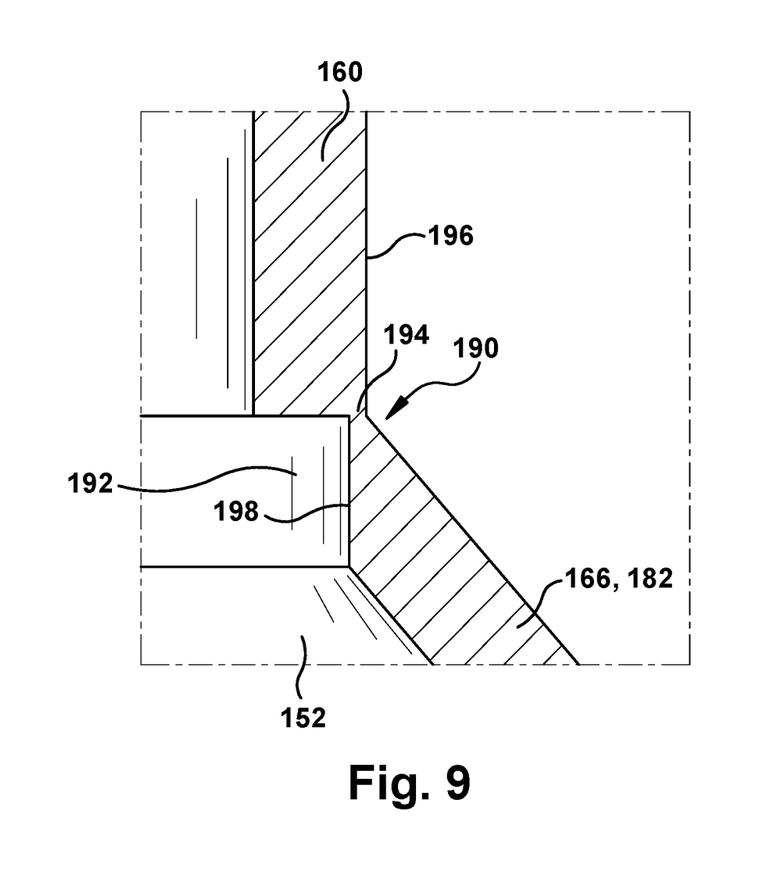
FIG. 9 shows an enlarged cross-sectional view of a removable cap of the test feature FIGS. 5 and 7 according to an embodiment of the disclosure.

Metal powder sample capsule 150 may have an exterior surface that is defined by any of a variety of geometric forms. In one embodiment, shown in FIGS. 5-6, metal powder sample capsule 150 has an exterior surface 164 defined by a first tapered end 166 separated from a second tapered end 168 by an elongated body 170. As used herein, "elongated" indicates a length that spaces the larger portions of tapered ends 166, 168 from one another. As shown, removable cap 160 may be positioned at first tapered end 166. In FIGS. 5 and 6, first tapered end 166 and second tapered end 168 may each include an exterior surface at least a portion of which is conical. That is, each end 166, 168 has a portion that is funnel shaped. Tapered ends 166, 168 are advantageous because they use less metal powder to build than, for example, a cylindrical body. In FIGS. 5 and 6, elongated body 170 has a cylindrical exterior surface 172. In other embodiments (not shown), ends 166, 168 and elongated body 170 may have a number of exterior side surfaces set at angles, i.e., such that they have polygonal cross-sections. In FIGS. 5 and 6, removable cap 160 may have a trapezoidal exterior (FIG. 5) (and trapezoidal cross-section). Alternatively, as shown in FIG. 9, removable cap 160 may include a cylindrical exterior (FIG. 7) (and close ended, tubular cross-section).

As shown in one example in FIG. 5, in one embodiment, metal powder sample capsule 150 of test feature 108 may include a planar test area 180 positioned on, e.g., elongated body 170 or another part of exterior surface 164. Planar test area 180 may be used for a number of purposes such as but not limited to: labeling during AM, and testing such as hardness testing or surface roughness testing of capsule 150 and therefore of production parts 102. For example, planar test area 180 may be evaluated for surface roughness testing using a profilometer measuring device (not shown). The measurement may be performed at planar test area 180 and/or on other parts of exterior surface 164 of the capsule. Although not shown for each embodiment, planar test area 180 may be applied to any of metal powder sample capsule 150 embodiments described herein (e.g., that of FIGS. 7-19).

Figure 7:
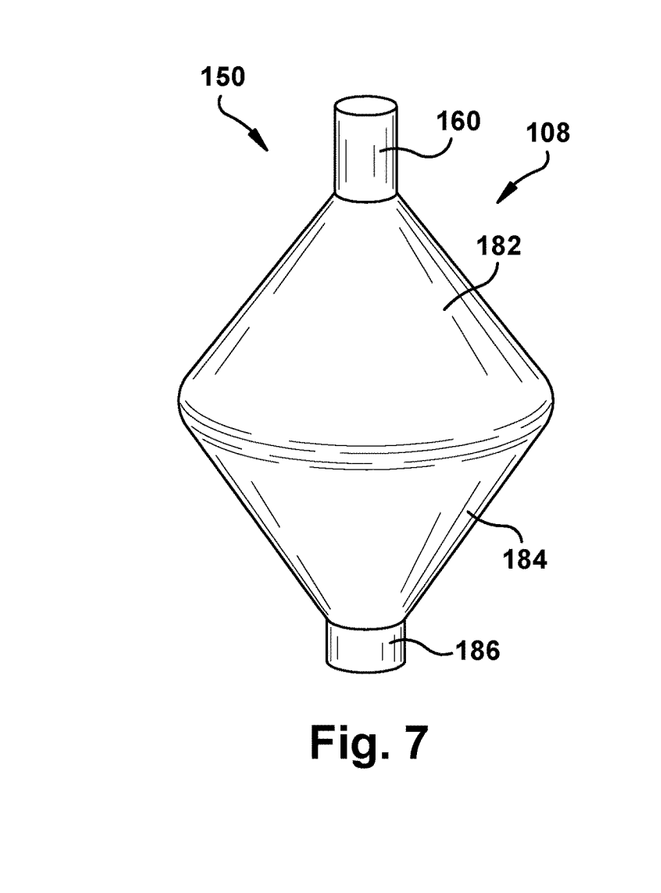
FIG. 7 shows a perspective view of a test feature according to an embodiment of the disclosure.
Figure 8:
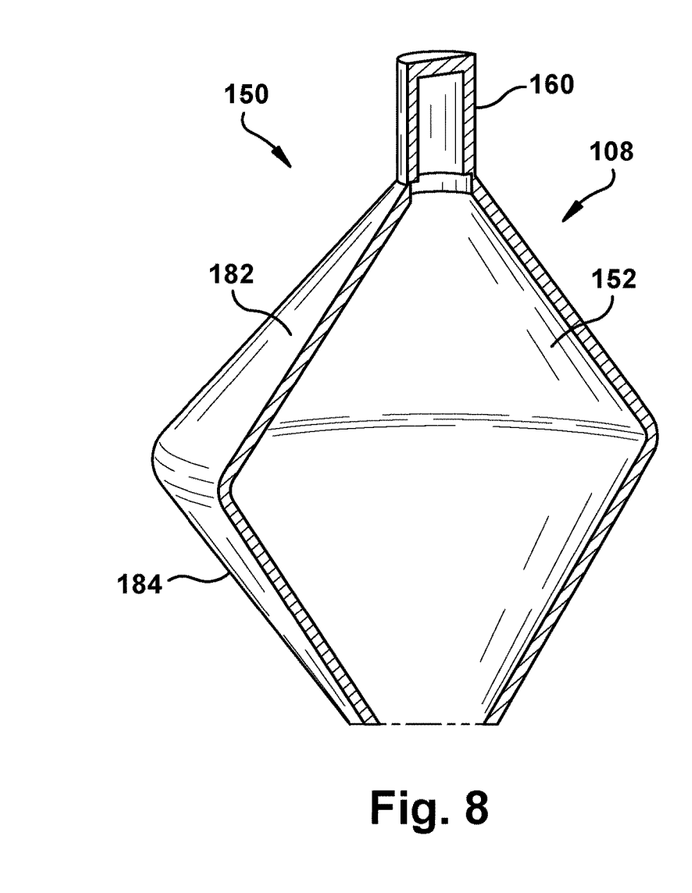
FIG. 8 shows a perspective, cross-sectional view of the test feature of FIG. 7 according to an embodiment of the disclosure.

In another embodiment, shown in FIGS. 7 and 8, metal powder sample capsule 150 of test feature 108 may have a three-dimensional rhombus body. That is, metal powder sample capsule 150 may have a first tapered end 182 and a second tapered end 184 that meet at their widest portion to form chamber 152, like two funnels. Tapered ends 182, 184 may take any form previously described relative to tapered ends 166, 168 from FIGS. 5-6. Removable cap 160 is provided at one end of one of the tapered ends, 182 as shown. In the FIGS. 7 and 8 embodiments, removable cap 160 may have a cylindrical exterior (FIG. 7) (and close ended, tubular cross-section).

As also shown in FIGS. 5-7, in one embodiment, a metal powder sample capsule 150 may include a single, manually breakable support 186 extending from one end, i.e., second tapered end 168, 184, of the capsule to support metal powder sample capsule 150 on build platform 118. Support 186 is sized and shaped such that it can be removed from build platform 118 by application of manual bending force, i.e., using a human hand with no or only small hand tools. Hence, support 186 holds the capsule in position on build platform 118 but allows removal rapidly and with no-wire EDM required. Only one support 186 is necessary.

As shown in the enlarged cross-sectional view of FIG. 9, removable cap 160 (as in either embodiments of FIGS. 5-8) may be coupled to chamber 152 by a stress concentration area 190 configured to manually break, allowing removal of removable cap 160 and creation of an opening 192 to the chamber. In the FIG. 9 embodiment, stress concentration area 190 includes a lateral overlap 194 between an outer edge 196 of removable cap 160 and an inner edge 198 of opening 192 of chamber 152. Stress concentration area 190 is sized and shaped such that removable cap 160 can be removed from chamber 152 by application of manual bending force, i.e., using a human hand with no or only small hand tools. Hence, stress concentration area 190 holds the cap in position on chamber 152 but allows removal rapidly and safely to allow removal of metal powder 154 (FIG. 6).

Figure 10:
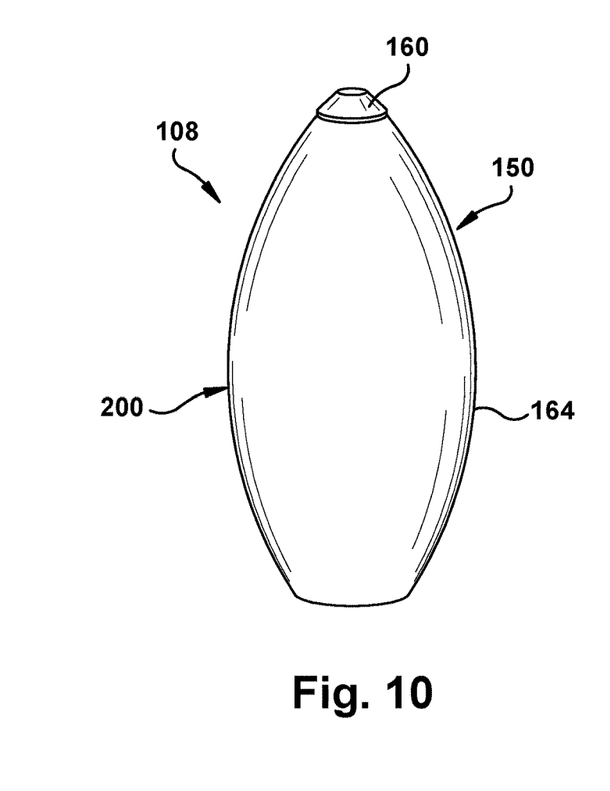
FIG. 10 shows a perspective view of a test feature according to an embodiment of the disclosure.
Figure 11:
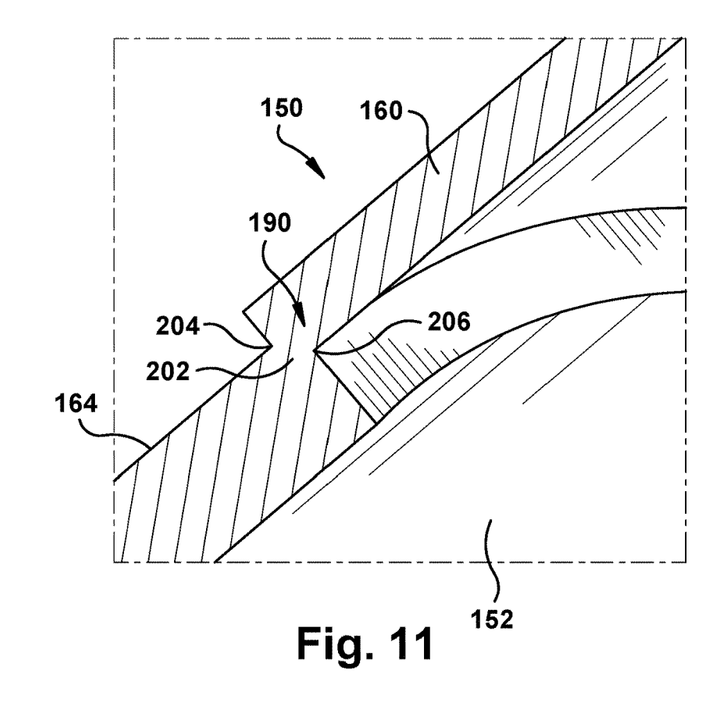
FIG. 11 shows an enlarged cross-sectional view of a portion of a removable cap of the test feature of FIG. 10 according to an embodiment of the disclosure.
Figure 12:
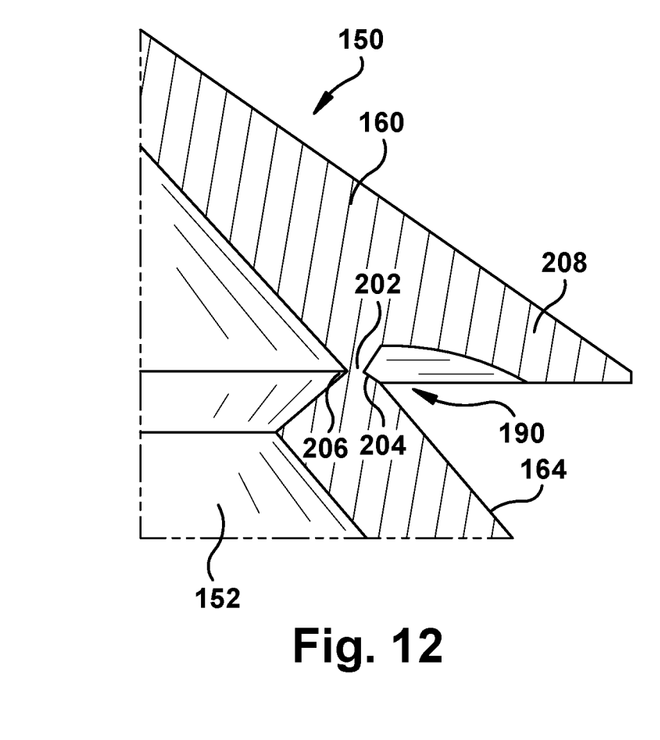
FIG. 12 shows an enlarged cross-sectional view of a portion of a removable cap of the test feature FIG. 10 according to another embodiment of the disclosure.
Figure 13:
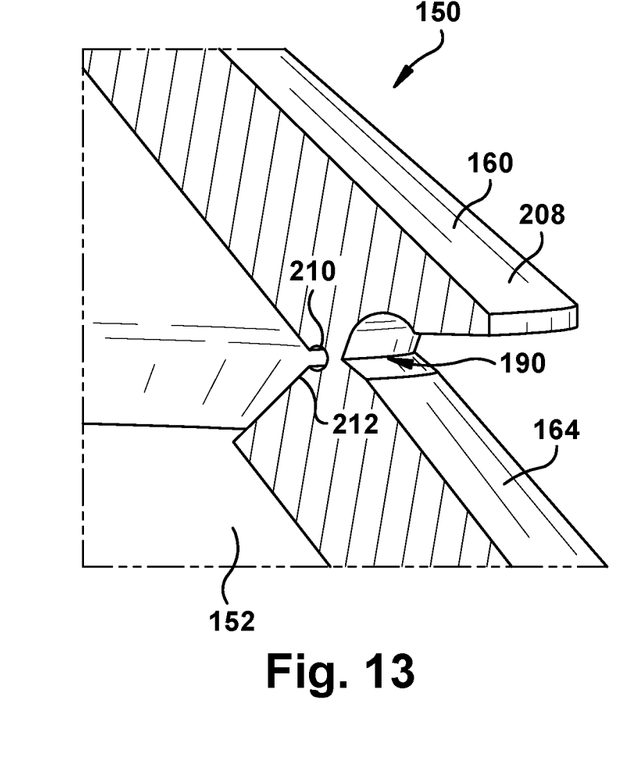
FIG. 13 shows an enlarged cross-sectional view of a portion of a removable cap of the test feature of FIG. 10 according to yet another embodiment of the disclosure.

Referring to FIG. 10, a perspective view of another embodiment of test feature 108 including metal powder sample capsule 150 is shown. In this embodiment, metal powder sample capsule 150 may have exterior surface 164 defined by a bulbous body 200. In this example, exterior surface 164 is somewhat tear shaped—narrower at ends with rounded middle section. Here, also, removable cap 160 has an upwardly convex configuration, i.e., like an upside down plate. As shown in the enlarged cross-sectional view of FIG. 11, in this embodiment, stress concentration area 190 may include a diagonal overlap 202 (e.g., angled relative to horizontal) between an outer edge corner 204 of chamber 152, i.e., wall of chamber 152, and an inner edge corner 206 of opening 192 of chamber 152. Again, stress concentration area 190 is sized and shaped such that removable cap 160 can be removed from chamber 152 by application of manual bending force, i.e., using a human hand with no or only small hand tools. FIGS. 12 and 13 show enlarged cross-sectional views of alternative embodiments of removable cap 160 and stress concentration area 190. FIGS. 12 and 13 both show removable cap 160 having an upwardly convex configuration and including an overhang 208, which may be grasped by a human hand or small tool to assist in removal of the cap. Stress concentration area 190 in FIG. 12 is similar to that of FIG. 11. In FIG. 13, however, a bevel 210 may be provided along an inner facing surface 212 of the stress area. Bevel 210 may be sized and shaped to assist in removal of removable cap 160, e.g., by allowing fine tuning of the necessary force.

Figure 14:
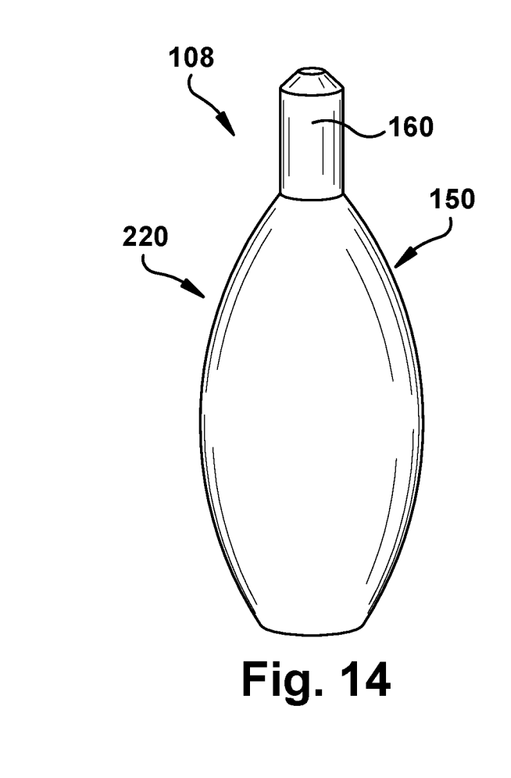
FIG. 14 shows a perspective view of a test feature according to an embodiment of the disclosure.
Figure 15:
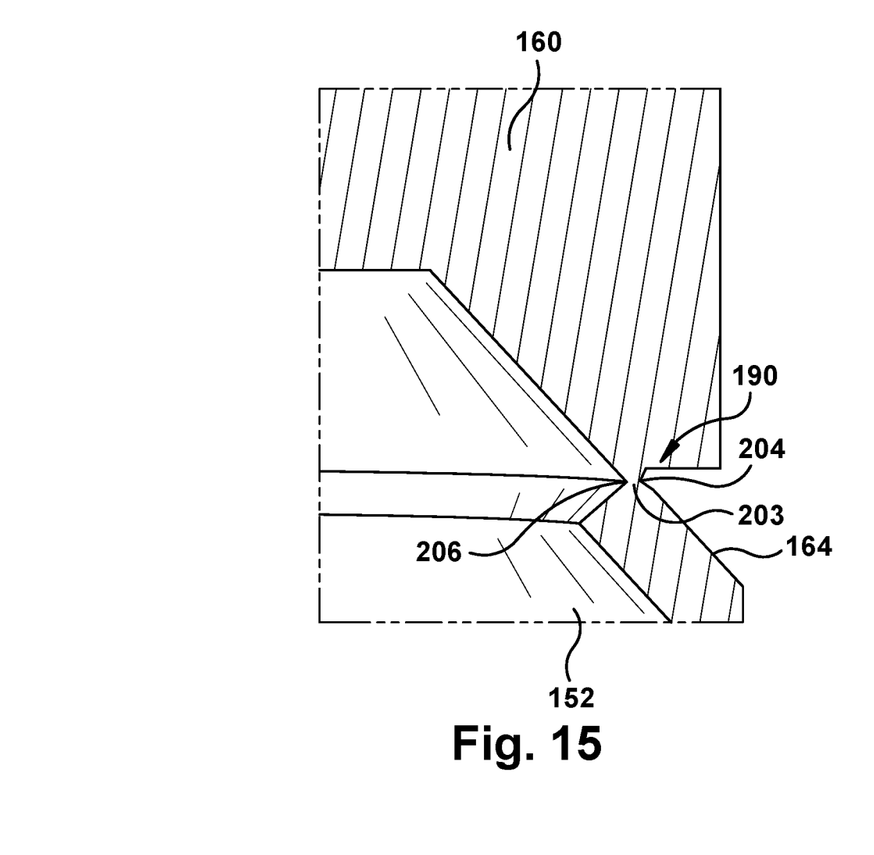
FIG. 15 shows an enlarged cross-sectional view of a portion of a removable cap of the test feature of FIG. 14 according to an embodiment of the disclosure.

Referring to FIG. 14, a perspective view of another embodiment of test feature 108 including metal powder sample capsule 150 is shown. In this embodiment, metal powder sample capsule 150 may have an exterior surface defined by a bulbous body 220, e.g., tear-shaped, narrower at ends with rounded middle section but not as round as in FIG. 10. As shown in FIG. 15, in this embodiment, stress concentration area 190 includes a lateral overlap 203 between an outer edge corner 204 of chamber 152, i.e., wall of chamber 152, and an inner edge corner 206 of opening 192 of chamber 152. Again, stress concentration area 190 is sized and shaped such that removable cap 160 can be removed from chamber 152 by application of manual bending force, i.e., using a human hand with no or only small hand tools. Removable cap 160, in FIGS. 14 and 15, may have a cylindrical exterior surface but is solid internally, compared to a hollow version as in FIGS. 8 and 9.

Figure 16:
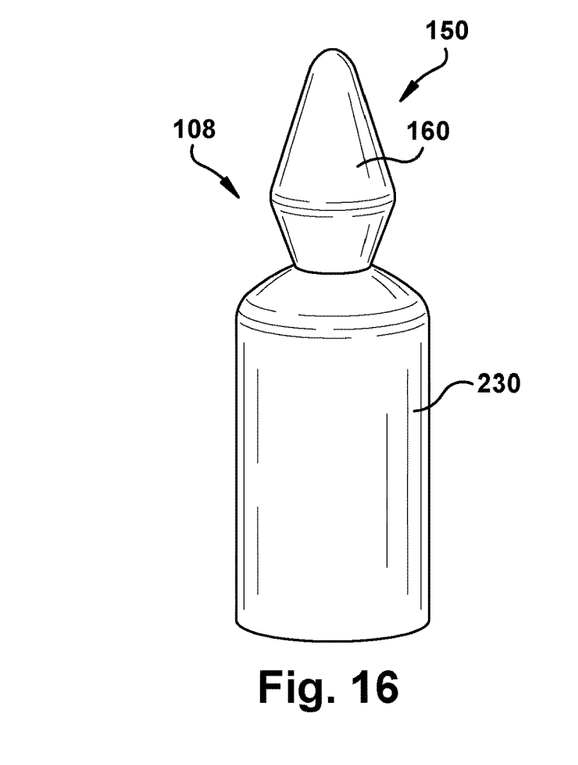
FIG. 16 shows a perspective of test feature according to another embodiment of the disclosure.
Figure 17:
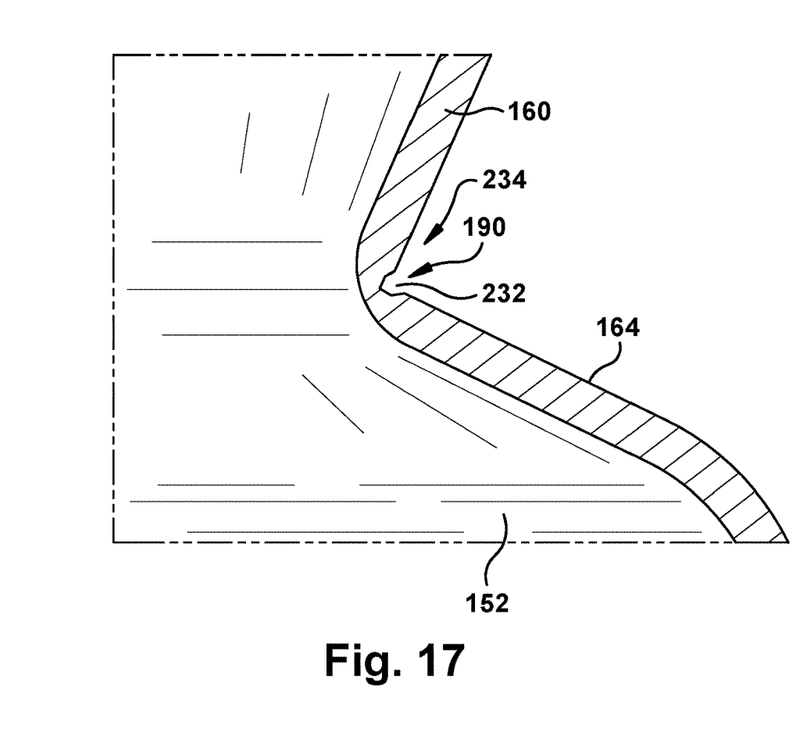
FIG. 17 shows an enlarged cross-sectional view of a portion of a removable cap of the test feature of FIG. 16 according to an embodiment of the disclosure.

Referring to FIG. 16, a perspective view of another embodiment of test feature 108 including metal powder sample capsule 150 is shown. In this embodiment, metal powder sample capsule 150 may have exterior surface 164 defined by a cylindrical body 230, e.g., bottle-shaped with cylindrical body with a narrowing end near removable cap 160. Removable cap 160 may have a 3D rhombus shape, similar to the capsule of FIGS. 7 and 8 but truncated where it meets chamber 152. As shown in the enlarged cross-sectional view of FIG. 17, in this embodiment, stress concentration area 190 includes a bevel 232 in a corner 234 between removable cap 160 and chamber 152. Again, stress concentration area 190 and bevel 232 may be sized and shaped such that removable cap 160 can be removed from chamber 152 by application of manual bending force, i.e., using a human hand with no or only small hand tools.

Regardless of embodiment, test feature 108 including metal powder sample capsule 150 provides for a full comprehensive analysis for powder chemistry to particle size composition, surface roughness, surface hardness and metallography studies to successfully track powder and metal compliance of the AM specifications and part quality. The analysis can be used on new and reused metal powder. The evaluation can be carried out for metal powder inside metal powder sample capsule 150 as well as the capsule's exterior surface metal. The metal powder captured with the capsule is sealed from the external environment. Further, the capsule can be sized to capture a predetermined amount of powder, e.g., an exact amount needed for testing, and is environmental and health safety (EHS) compliant for handling powder processes and transportation. The different geometries described herein can be selected to accommodate different positioning and different production parts 102. The exterior surface of the capsule is guaranteed to have as-printed powder metal properties identical to production parts 102. Further, the geometries for metal powder sample capsule 150 described herein are configured to avoid the need for internal or external supports. For example, all surfaces are made at no greater than a 45° angle relative to horizontal. Further, through the use of those embodiments that employ a single support 186 (FIGS. 5-8), no tools are required to remove test feature 108 from build platform 118 (FIGS. 3-4).

Figure 18:
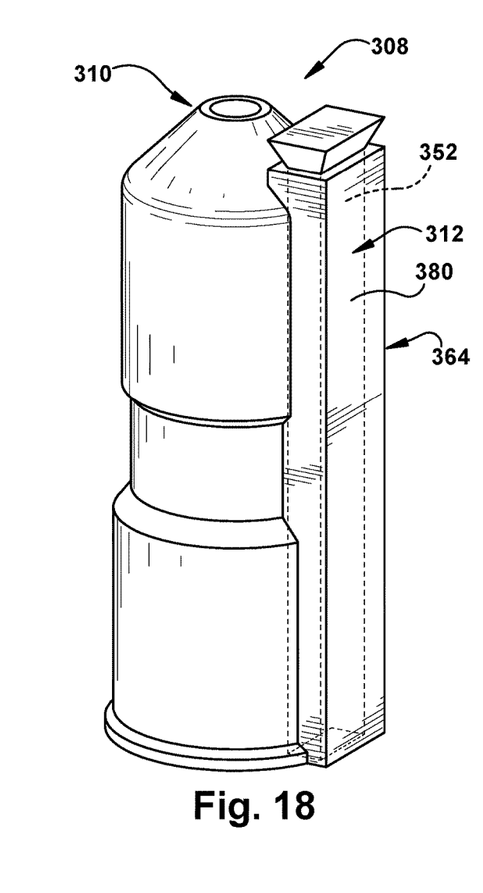
FIG. 18 shows a perspective view of a test feature according to an embodiment of the disclosure.
Figure 19:
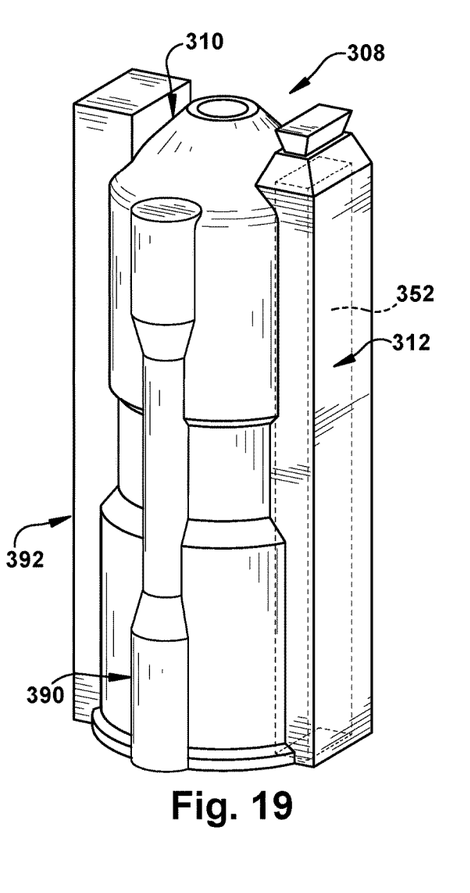
FIG. 19 shows a perspective view of a test feature according to another embodiment of the disclosure.

Turning to the perspective views of FIGS. 18 and 19, a test feature 308 according to additional embodiments of the disclosure is shown. In this embodiment, test feature 308 may include a quality control (QC) part 310. QC part 310 is structured to be identical, except as described herein, to production part 102 (FIG. 3) formed during the same additive manufacturing process on build platform 118 (FIG. 3). In this example, QC part 310, and hence production part 102 (FIG. 3), is in the form of a fuel nozzle, but it can be any structure. Test feature 308 may also include, as shown in FIG. 18, at least one test element including a metal powder sample capsule 312 integrally coupled to QC part 310 and including a chamber 352 for capturing unfused powder from the metal powder additive manufacturing. As shown in FIG. 18, the at least one test element including metal powder sample capsule 312 is integrally coupled to QC part 310. Hence, QC part 310 is identical to production part 102 except the at least one test element. In one embodiment, metal powder sample capsule 312 and QC part 310 have a height identical to a height of production part 102 (FIG. 3). In this fashion, QC part 310 fully mimics production part 102, and capsule 312 may capture unfused metal powder along an entire height of production part 102 (FIG. 3). As previously described herein, metal powder sample capsule 312 may include a planar test area 380 on a portion of an exterior surface 364 thereof. Planar test area 380 may provide the same functionality as planar test area 180 previously described. Metal powder sample capsule 312 may also include a removable cap 360 closing an end of a chamber 352 thereof. Removable cap 360 can take on any form previously described herein. Removable cap 360 may have an uppermost point that is at the same height as a topmost point of QC part 310, or removable cap 360 may extend above a topmost point of QC part 310 to ensure unfused powder at that level of QC part 310 is encapsulated in the capsule.

Referring to FIG. 19, test feature 308 may also include additional test elements. For example in FIG. 19, a tensile bar 390 is integrally coupled to QC part 310. Tensile bar 390 may have any geometric form now known or later developed for mechanical property testing of materials, e.g., a bar with wider ends with narrower waist. In another example, test feature 308 includes a test bar 392 integrally coupled to QC part 310. Test bar 392 may have any cross-sectional shape desired for testing, e.g., polygonal, circular, tubular etc. Test bar 392 is equal to the height of production part 102 and may be added to build platform 118 (FIG. 3) to record, for example, downtime witness features and to measure surface roughness.

Test feature 308 allows a build platform 118 (FIGS. 3-4) to have various test elements to evaluate such as aspects as: build quality, laser parameter configuration, lack of fusion, linear defects, powder quality, downtime, roughness, mechanical properties, etc. Test feature 308 is a representative sample because it uses the same printing parameters (up skin, down skin, hatch, etc.) as production part 102 (FIG. 3). If test elements are formed separately, as shown in FIG. 1, they take up room on build platform 12 and may reduce the quantity of production parts 102 printed on the platform and increase the time it takes to produce parts. Test feature 308 reduces the amount of space required, increasing space for production parts 102 and increase the amount of time AM system 100 (FIG. 2) can make production parts 102 rather than test features.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate +/−10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A test feature formed during metal powder additive manufacturing of a production part, the test feature comprising:
a metal powder sample capsule including a chamber for capturing unfused powder from the metal powder additive manufacturing, wherein the metal powder sample capsule is integrally coupled to a quality control (QC) part to form a unitary entity that is otherwise identical to the production part, the QC part and the production part formed during the same metal powder additive manufacturing, wherein the metal powder sample capsule and the QC part have a height identical to a height of the production part;
a tensile bar integrally coupled to the QC part to form the unitary entity;
a test bar integrally coupled to the QC part to form the unitary entity; and
a removable cap closing an end of the chamber.

2. The test feature of claim 1, wherein the metal powder sample capsule has an exterior surface defined by a first tapered end separated from a second tapered end by an elongated body, the removable cap positioned at the first tapered end.

3. The test feature of claim 2, further comprising a single, manually breakable support extending from the second tapered end to support the metal powder sample capsule on a build platform.

4. The test feature of claim 2, further comprising a planar test area positioned on the elongated body.

5. The test feature of claim 2, wherein the first tapered end and the second tapered end each include an exterior surface at least a portion of which is conical, and the elongated body has a cylindrical exterior surface.

6. The test feature of claim 1, further comprising a single, manually breakable build platform support extending from one end of the metal powder sample capsule to support the metal powder sample capsule on a build platform.

7. The test feature of claim 1, further comprising a planar test area positioned on an exterior surface of the metal powder sample capsule.

8. The test feature of claim 1, wherein the metal powder sample capsule has an exterior surface defined by one of: a bulbous body, a cylindrical body, and a three-dimensional rhombus body.

9. The test feature of claim 1, wherein the metal powder sample capsule includes a planar test area on an exterior surface thereof.

10. The test feature of claim 1, wherein the removable cap is coupled to the chamber by a stress concentration area configured to manually break, allowing removal of the cap and creation of an opening to the chamber.

11. A test feature formed during metal powder additive manufacturing of a production part, the test feature comprising:
   a quality control (QC) part; and
   at least one test element including a metal powder sample capsule integrally coupled to the QC part to form a unitary entity and including a chamber for capturing unfused powder from the metal powder additive manufacturing,
   wherein the QC part is identical to the production part excepting the at least one test element, the QC part and the at least one test element formed during the same metal powder additive manufacturing as the production part, wherein the metal powder sample capsule includes a removable cap closing an end of the chamber, wherein the metal powder sample capsule and the QC part have a height identical to a height of the production part, wherein the at least one test element further includes a tensile bar integrally coupled to the QC part to form the unitary entity, wherein the at least one test element further includes a test bar integrally coupled to the QC part to form the unitary entity, and wherein the metal powder sample capsule includes a planar test area on an exterior surface thereof.

* * * * *